United States Patent [19]

Romano

[11] Patent Number: 4,512,930

[45] Date of Patent: Apr. 23, 1985

[54] PROCESS FOR SYNTHESIZING CARBONIC ACID ESTERS DERIVED FROM UNSATURATED ALCOHOLS AND POLYHYDRIC ALCOHOLS

[75] Inventor: Ugo Romano, Vimercate, Italy

[73] Assignee: ANIC, S.p.A., Palermo, Italy

[21] Appl. No.: 371,670

[22] Filed: Apr. 26, 1982

[30] Foreign Application Priority Data

May 21, 1981 [IT] Italy ............... 21884 A/81

[51] Int. Cl.³ .............................. C07C 68/06
[52] U.S. Cl. ..................... 260/463; 526/314
[58] Field of Search ......................... 260/463

[56] References Cited

U.S. PATENT DOCUMENTS

| | | | |
|---|---|---|---|
| 2,384,115 | 9/1945 | Muskat et al. | 260/463 |
| 2,789,968 | 5/1957 | Reynolds et al. | 260/463 X |
| 3,632,828 | 1/1972 | Frevel et al. | 260/463 |
| 3,642,858 | 2/1972 | Frevel et al. | 260/463 |
| 3,784,578 | 1/1974 | Swodenk et al. | 260/463 X |
| 4,062,884 | 12/1977 | Romano et al. | 260/463 |
| 4,144,262 | 3/1979 | Stevens | 260/463 |
| 4,273,726 | 6/1981 | Altnglu | 260/463 |
| 4,307,032 | 12/1981 | Krimm et al. | 260/463 |
| 4,349,486 | 9/1982 | Brunelle et al. | 260/463 |

FOREIGN PATENT DOCUMENTS

| | | | |
|---|---|---|---|
| 0035304 | 9/1981 | European Pat. Off. | |
| 0072325 | 2/1983 | European Pat. Off. | 260/463 |
| 2749754 | 5/1979 | Fed. Rep. of Germany | 260/463 |

OTHER PUBLICATIONS

Mark and Gaylord (eds.), Encyclopedia of Polymers and Technology, vol. 10, (1969) p. 712, Interscience Pub. N.Y.

*Primary Examiner*—Donald G. Daus
*Assistant Examiner*—Diana G. Rivers
*Attorney, Agent, or Firm*—Morgan, Finnegan, Pine, Foley & Lee

[57] ABSTRACT

The application relates to a process for synthesizing unsaturated carbonic acid esters from polyhydric alcohols, which are reacted with alkyl carbonates and unsaturated alcohols in the presence of a basic catalyst, which can be chosen from sodium hydroxide, sodium carbonate, sodium alcoholate, organic bases and basic ion exchange resins.

8 Claims, No Drawings

PROCESS FOR SYNTHESIZING CARBONIC ACID ESTERS DERIVED FROM UNSATURATED ALCOHOLS AND POLYHYDRIC ALCOHOLS

This invention relates to a process for synthesizing carbonic esters from polyhydric alcohols, consisting of reacting a dialkyl carbonate with an unsaturated alcohol and the relevant polyhydric alcohol in the presence of a basic catalyst. The product thus obtained is then used for postmodification of polymerisation reactions in order to produce valuable derivatives of various uses as described in the European Pat. Appln. published on Sept. 9, 1981 No. 35304 in the name of the same applicant.

Bis allyl carbonates of glycols and/or polyglycols are known to be commonly prepared by reacting allyl chloroformate with the glycol, or alternatively the glycol-bis-chloroformate with the allyl alcohol, the reaction always taking place in the presence of an acceptor for the hydrochloric acid which is released, as described for example in the U.S. Pat. Nos. 2,370,565 and 2,592,058.

The reactions stated are such that the products obtained are frequently coloured when in the crude state, and are thus unsuitable for immediate use in that which is considered one of the main fields of application of these compounds, namely raw materials for forming organic glass substitutes for optical purposes.

The purification comprises stages such as decoloration and/or distillation under reduced pressure, which considerably affect the economics of the process and a priori cannot ensure the subsequent good quality of the product.

In this respect, the presence of chloroformate among the starting materials leads to a constant presence of chlorinated impurities in the final products even after purification, and these impurities characterize the specific properties of the product, so as to make the subsequent treatment which precedes their practical use sometimes problematic.

The aforesaid European Pat. Appln. relates to an improved process for synthesising allyl carbonates of polyhydric alcohols, mainly glycols, which enables the final products to be obtained without any of the aforesaid drawbacks. The process comprises reacting together the starting substrates (polyols and allyl carbonate) at a temperature of between 50° and 150° C. and at a pressure variable between atmospheric pressure and 10 mmHg.

It has now been found, and constitutes the subject matter of the present invention, that it is possible to obtain the same products by starting directly from the precursors of allyl carbonate, these being thus placed directly in contact with the relevant polyhydric alcohol.

In fact, a surprising advantage of the process according to the present invention is that in synthesising the final product it can start not only from the allyl alcohol but from any other unsubstituted alcohol, the range of final products, i.e. useful products, thus being considerably increased.

Thus the unsaturated alcohols used can be chosen from allyl alcohol, allyl carbinol, methallyl alcohol, crotyl alcohol, 3-buten-2-ol and 2-methyl-3-buten-2-ol. The alkyl carbonate is chosen from dimethyl carbonate, diethyl carbonate, dipropyl carbonate, dibutyl carbonate and dibenzyl carbonate. The reaction between the starting substances takes place at a temperature of between 50° and 150° C. and at a pressure variable between 10 mmHg and atmospheric pressure. The starting compounds are brought into contact in the presence of a basic catalyst, which is introduced in a quantity variable between 0.1 ppm and 1% by weight with respect to the alcohol.

The molar ratio of the unsaturated alcohol to the polyhydric alcohol varies between 2 and 40, whereas the molar ratio of the unsaturated alcohol to the alkyl carbonate varies between 2 and 10.

The polyhydric alcohols used can be chosen from a wide range, for example ethylene glycol, propylene glycol, diethylene glycol, tetraethylene glycol, butanediol, hexanediol, neopentyl glycol, glycerol, trimethylolpropane, pentaerythritol etc., either alone or in mixture.

The catalyst itself can be chosen from NaOH, $Na_2CO_3$, sodium alcoholate, organic bases and basic ion exchange resins. The reaction can be carried out using commercially available products as the starting substances without further purification.

The final products are absolutely colourless and free from those impurities which lead to the disadvantages of the products obtained according to the known art.

With regard to the nature and composition of the final products, the result of the process according to the present invention does not differ from the description of the patent application heretofore mentioned, and reference should be made thereto for a better understanding of said final products and their specific uses.

The description given hereinafter will therefore be limited to some examples given simply for illustrating the invention, but without limiting its scope.

EXAMPLE 1

2320 g (40 moles) of allyl alcohol, 1800 g (20 moles) of dimethyl carbonate, 170 g (1.6 moles) of diethylene glycol and sodium methylate as catalyst to the extent of 0.1% of the feed were placed in a 5000 cc flask which was heated by means of a temperature-controlled oil circulation jacket, provided with a temperature control system and a system for withdrawing liquid samples, and surmounted by a 1" distillation column comprising 30 perforated plates and a liquid dividing head.

The mixture was heated at atmospheric pressure to boiling (approximately 85° C. at the bottom) and the methanol-dimethylcarbonate azeotrope was distilled off as overhead (approximately 63° C.).

The column reflux was controlled during the course of the test so that no allyl alcohol appeared in the overhead product. The first stage of the reaction, consisting of removing the methanol formed during the reaction, lasted approximately 5 hours.

During this period, a fraction was collected as overhead having a weight of 1020 g, containing 70% by weight of methanol and 30% by weight of dimethylcarbonate.

A fraction of 969 g was then distilled off under constant reflux ratio (2.5), and contained 63.5% of allyl alcohol with 33.7% of methanol and 2.8% of dimethyl carbonate. During the course of this reaction stage, which lasted 4 hours, the pressure varied from 760 to 150 mmHg so as not to exceed 120°–130° C. at the bottom of the flask.

During the final reaction stage, most of the diallyl carbonate was distilled off under reduced pressure (100 mmHg), and only at the end was the pressure reduced to 2 mmHg.

1860 g of diallyl carbonate were obtained as overhead, containing less than 1% of allyl alcohol and methyl allyl carbonate, the bottom product weighing 440 g and comprising both the reaction product and the catalyst.

This latter was removed by washing with water, and the moist product was dried by stripping under vacuum.

438 g of product was obtained, consisting of essentially of diethylene glycol bis allyl carbonate (approximately 91%) with small quantities of diallyl carbonate (0.2%) and diethylene glycol oligocarbonates likewise terminating in carbonic allyl groups (8.8%).

The dimethyl carbonate, allyl alcohol and diallyl carbonate were used for subsequent syntheses.

EXAMPLE 2

The reaction was carried out in a substantially similar manner to example 1, except that the diethylene glycol was replaced by neopentyl glycol (approximately 167 g, equal to 1.6 moles).

435 g of product were obtained consisting essentially of neopentyl glycol bis allyl carbonate (89%) with 0.6% of diallyl carbonate and 10.4% of neopentyl glycol oligocarbonates likewise terminating in carbonic allyl groups.

EXAMPLE 3

The reaction was carried out in a similar manner to example 1, except that the diethylene glycol was replaced by triethylene glycol (220 g, equal to 1.5 moles). 476 g of product were obtained consisting of triethylene glycol bis allyl carbonate (93% with 0.4% of diallyl carbonate and 6.6% of diethylene glycol oligocarbonates which were bis allyl terminated.

EXAMPLE 4

The reaction was carried out in a similar manner to example 1, but using butanediol (162 g, equal to 1.8 moles).

454 g of product were obtained consisting of butanediol bis allyl carbonate (84%) with diallyl carbonate (0.5%) and butanediol oligocarbonate bis allyl terminated (15.5%).

EXAMPLE 5

The reaction was carried out following the procedure described in example 1, except that the dimethyl carbonate was replaced by diethyl carbonate (2120 g, equal to 18 moles), the allyl alcohol was replaced by allyl carbinol (3-buten-1-ol) (2880 g, equal to 40 moles), and the sodium methylate was replaced by sodium ethylate.

480 g of product were obtained of which 90% consisted of diethylene glycol bis butenyl carbonate, 1% consisted of dibutenyl carbonate, and 9% consisted of diethylene glycol oligocarbonate bis butenyl terminated.

In this case, during the reaction both the ethanol produced by the transesterification and the dibutenyl carbonate were recovered, this latter being reused for subsequent synthesis as the diethyl carbonate conversion was practically total.

EXAMPLE 6

The reaction was carried out as in example 5, except that the diethylene glycol was replaced by neopentyl glycol (167 g, equal to 1.6 moles).

455 g of product were obtained consisting of neopentyl glycol bis butenyl carbonate (89% with 1.2% of dibutenyl carbonate and 9.8% of neopentyl glycol oligocarbonate bis butenyl terminated.

I claim:

1. A process for synthesizing unsaturated bis-carbonates of polyhydric alcohols consisting essentially of the step of reacting an unsaturated alcohol selected from the group consisting of allyl alcohol, allyl carbinol, methallyl alcohol, crotyl alcohol, 3-buten-2-ol and 2-methyl-3-buten-2-ol with an alkyl carbonate selected from the group consisting of dimethyl carbonate, diethyl carbonate, dipropyl carbonate, dibutyl carbonate and dibenzyl carbonate and a polyhydric alcohol selected from the group consisting of ethylene glycol, propylene glycol, diethylene glycol, triethylene glycol, tetraethylene glycol, butanediol, hexanediol, neopentyl glycol, glycerol, trimethylol propane, and pentaerythritol or a combination thereof, wherein the molar ratio of unsaturated alcohol to polyhydric alcohol is between about 2 and and about 40 and the molar ratio of said unsaturated alcohol to said alkyl carbonate is between about 2 and about 10, said reaction taking place in the presence of an alkaline catalyst selected from the group consisting of sodium hydroxide, sodium carbonate and organic bases.

2. A process according to claim 1 wherein said alkaline catalyst is an organic base.

3. A process according to claim 2 wherein said organic base is sodium alcoholate.

4. A process according to claim 2 wherein said organic base is a basic ion exchange resin.

5. A process according to claim 1 wherein said alkaline catalyst is present in a quantity from about one ppm to about one percent by weight of the alcohol.

6. A process according to claim 1 wherein said reaction is carried out at a temperature of between about 50° C. and about 150° C.

7. A process according to claim 1 wherein said reaction is carried out at a pressure of between about 10 mmHg and about atmospheric pressure.

8. A process for synthesising diallyl carbonates of polyhydric alcohols consisting essentially of the step of reacting:
   (i) an unsaturated alcohol selected from the group consisting of allyl alcohol and allylcarbinol; and
   (ii) a dialkyl carbonate selected from the group consisting of dimethyl carbonate and diethyl carbonate; and
   (iii) a dihydric alcohol selected from the group consisting of diethylene glycol, triethylene glycol, butanol and neopentylglycol, wherein said reaction takes place in the presence of an alkaline catalyst selected from the group consisting of sodium hydroxide, sodium carbonate and sodium alcoholate, at a pressure between 10 mmHg and 1 atmosphere and a temperature between about 50° C. and about 150° C. and wherein the molar ratio of unsaturated alcohol to alkyl carbonate is between about 2 and about 10, the molar ratio of unsaturated alcohol to dihydric alcohol is between about 2 and about 40, and said alkaline catalyst is present in a quantity between about one ppm to about 1 percent in relation to the alcohol.

* * * * *